United States Patent [19]

Tsao

[11] 4,267,333
[45] May 12, 1981

[54] PREPARATION OF 2-TRIFLUOROMETHYL CINCHONINIC ACIDS

[75] Inventor: Hsiang-Wei Tsao, Lansdale, Pa.

[73] Assignee: Union Carbide Agricultural Products Company, Inc., Ambler, Pa.

[21] Appl. No.: 78,922

[22] Filed: Sep. 26, 1979

[51] Int. Cl.³ .................................... C07D 215/50
[52] U.S. Cl. .......................... 546/170; 562/442; 562/451
[58] Field of Search ............................ 546/170

[56] References Cited

U.S. PATENT DOCUMENTS

| | | | |
|---|---|---|---|
| 1,181,485 | 5/1916 | Schwabe | 546/170 |
| 1,197,462 | 9/1916 | Dohrn | 546/170 |
| 1,816,003 | 7/1931 | Busch | 546/170 |
| 2,220,086 | 11/1940 | Dohrn et al. | 546/170 |
| 2,579,420 | 12/1951 | Coles | 546/170 |
| 3,574,840 | 4/1971 | Riviere et al. | 546/170 |
| 4,009,020 | 2/1977 | Starke et al. | 71/76 |

OTHER PUBLICATIONS

Dey et al.; Jour. of Het. Chem.; vol. 2; pp. 113-119, (1965).

Pinder et al.; J. Med. Chem., vol. 11, pp. 267-269, (1968).

*Primary Examiner*—Mary C. Lee
*Attorney, Agent, or Firm*—Dale Lynn Carlson

[57] ABSTRACT

2-Trifluoromethyl cinchoninic acids can be prepared in high yields by reaction of an alkali metal 2-aminophenylglyoxylate and 1,1,1-trifluoroacetone in the presence of a weak acid and a metal salt of a weak acid. Preferably reaction is effected by first hydrolyzing isatin, or a substituted isatin, in the presence of an alkali metal hydroxide to produce the alkali metal 2-aminophenylglyoxylate, and then reacting this intermediate product with 1,1,1-trifluoroacetone without isolating it from the reaction medium.

30 Claims, No Drawings

PREPARATION OF 2-TRIFLUOROMETHYL CINCHONINIC ACIDS

FIELD OF THE INVENTION

This invention relates to a novel method of preparing 2-trifluoromethyl cinchoninic acids.

BACKGROUND OF THE INVENTION

2-Trifluoromethyl cinchoninic acid, and substituted 2-trifluoromethyl cinchoninic acids, are known plant growth regulating materials. Such compounds can be prepared, as disclosed by B. M. Pinder and A. Burger (*J. Med. Chem*, 11, pp 267–269 (1968)), by condensation of aniline, or a substituted aniline, with ethyl 4,4,4-trifluoroacetoacetate in the presence of polyphosphoric acid to produce a 2-trifluoromethyl-4-hydroxyquinoline from which the desired 2-trifluoromethyl cinchoninic acid can be obtained by two alternative procedures. In the first of such procedures, the 2-trifluoromethyl-4-hydroxyquinoline is brominated with phosphorus oxybromide to produce the corresponding 2-trifluoromethyl-4-bromoquinoline which is then reacted with n-butyllithium to produce a lithioquinoline which can in turn be treated with dry carbon dioxide to produce the desired 2-trifluoromethyl cinchoninic acid. In the second of such procedures, the 2-trifluoromethyl-4-hydroxyquinoline is chlorinated with phosphorus oxychloride and the resulting 2-trifluoromethyl-4-chloroquinoline is reacted with cuprous cyanide in N-methylpyrrolidone to convert it to the corresponding nitrile which is then hydrolyzed to the desired 2-trifluoromethyl cinchoninic acid. However, not only are both these procedures complex and involved, but they produce yields of only about 35% and involve the use of corrosive materials such as phosphorus oxybromide and phosphorus oxychloride as well as air- and water-sensitive materials such a butyllithium and copper cyanide.

2-Methylcinchoninic acid has been prepared, as disclosed in *Bull. Soc. Chem.*, France, 1956, 1294, by the reaction of isatin and acetone in 30 percent aqueous potassium hydroxide solution. However, it has been found that when isatin is reacted with 1,1,1-trifluoroacetone in an attempt to produce 2-trifluoromethyl cinchoninic acid in an analogous manner, the desired product cannot be obtained.

Although 2-trifluoromethyl cinchoninic acid can be obtained by hydrolyzing isatin in aqueous potassium hydroxide solution to form potassium 2-aminophenylglyoxylate and then reacting the latter product with 1,1,1-trifluoroacetone after adjusting the pH of the solution to 7 or below by means of a strong acid, the yields obtained by such process have been found not to exceed 40%.

SUMMARY OF THE INVENTION

In accordance with the present invention, it has been discovered that 2-trifluoromethyl cinchoninic acids can be prepared in high yields by reaction of an alkali metal 2-aminophenylglyoxylate and 1,1,1-trifluoroacetone in the presence of a weak acid and a metal salt of a weak acid.

Preferably reaction is effected by first hydrolyzing isatin, or a substituted isatin, in the presence of an alkali metal hydroxide to produce the alkali metal 2-aminophenyglyoxylate, and then reacting this intermediate hydrolysis product with 1,1,1-trifluoroacetone without isolating it from the reaction medium. The overall reaction can be illustrated by the following equation:

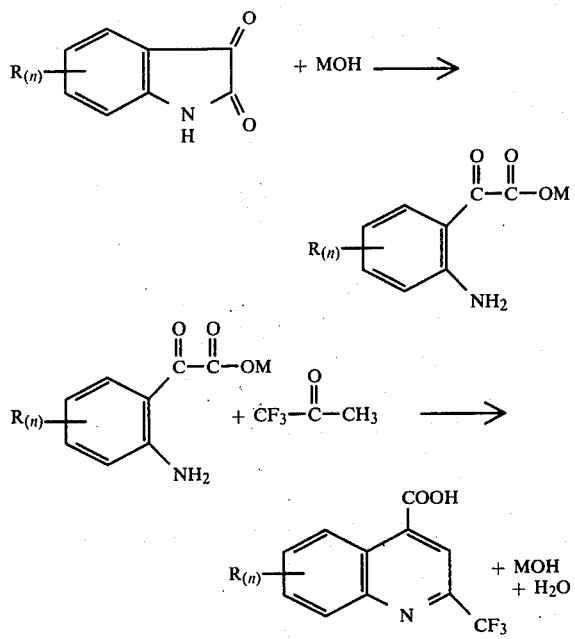

wherein R is selected from the group consisting of halogen, alkyl, aryl and alkoxy radicals, n is an integer having a value of from 0 to 2, and M is an alkali metal.

DETAILED DESCRIPTION

The isatin compounds which can be hydrolyzed to produce the alkali metal 2-aminophenylglyoxylates which are reacted with 1,1,1-trifluoroacetone in accordance with the present invention can be illustrated by the formula:

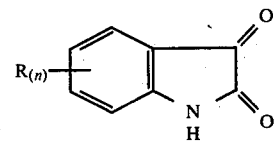

wherein R is selected from the group consisting of halogen, alkyl, aryl and alkoxy radicals, and n is an integer having a value of from 0 to 2. Preferably n is 0, i.e., an unsubstituted isatin is employed. When n is 1 or more, however, each R group present may be the same or different. When R is alkyl, aryl or alkoxy, it preferably contains from 1 to 6 carbon atoms; and when it is halogen, it is preferably chlorine. Typical substituted isatins include 5-methylisatin, 7-methylisatin, 5,7-dimethylisatin, 5-chloroisatin, 7-chloroisatin, 5,7-dichloroisatin, 5-methoxyisatin, 7-methoxyisatin, and 5,7-dimethoxyisatin. Such compounds are well known and can be prepared by direct substitution of isatin or by synthesis from para- or ortho, para-substituted anilines.

Hydrolysis of isatin, or a substituted isatin, to produce an alkali metal 2-aminophenylglyoxylate can be effected by simply dissolving the isatin compound in an aqueous solution containing at least one molar equivalent of an alkali metal hydroxide. An excess of the hydroxide, up to about a three molar excess, or higher, can be employed, if desired, to increase the rate of reaction. However, little advantage is obtained in employing more than a one molar excess of hydroxide. If desired, the solution can be heated to facilitate dissolution of the isatin compound. Other solvents, such as an alcohol, may be added to the solution if desired.

The alkali metal 2-aminophenylglyoxylate produced by hydrolysis of the isatin compound can be illustrated by the formula:

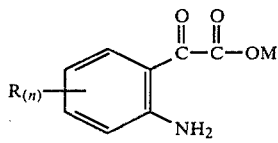

wherein R, n amd M are as above defined.

If desired, the alkali metal 2-aminophenylglyoxylate produced by the hydrolysis of isatin, or a substituted isatin, can be isolated from the reaction mixture before it is reacted with 1,1,1-trifluoroacetone. However, isolation is unnecessary and it is preferred to react these two materials in the same aqueous solution employed to hydrolyze the isatin compound.

After the alkali metal 2-aminophenylglyoxylate has been prepared (whether or not it has been isolated), it is reacted with 1,1,1-trifluoroacetone in the presence of a weak acid and a metal salt of a weak acid. Generally, equimolar amounts of each reactant are employed. Without wishing to be bound by any particular theory, it is believed that the acid acts to promote condensation of the 1,1,1-trifluoroacetone with the amino group of the 2-aminophenylglyoxylate compound, and the metal salt then acts to bring about ring closure to form the desired 2-trifluoromethyl cinchoninic acid.

Suitable acids which can be employed to effect reaction between the alkali metal 2-aminophenylglyoxylate and 1,1,1-trifluoroacetone are those acids which are soluble in the reaction medium and which have an ionization constant below $1 \times 10^{-2}$ but greater than $1 \times 10^{-7}$. Preferably, the acid employed has an ionization constant below $1 \times 10^{-4}$. Illustrative of the acids which can be employed are formic acid, acetic acid, propionic acid, butanoic acid, citric acid, succinic acid, phosphoric acid, and the like. While some product can be obtained employing a strong mineral acid, the yields obtained have not been found to exceed 40 percent, which yields are unsatisfactory for commercial operations.

In addition to a weak acid, it is necessary that a metal salt of a weak acid be present in the reaction mixture in order to obtain satisfactory yields of the desired product. While any metal salt which is soluble in the reaction mixture can be employed, it is preferable to employ an alkali metal salt. Although not absolutely necessary, it is often convenient to employ a metal salt of the same weak acid employed in the process. Such salt should be employed in an amount sufficient to maintain the pH of the reaction mixture at the desired level. For best results the pH should be maintained between 3 and 6, preferably between 4.5 and 5.5. Generally molar ratios of salt to acid of from 1:10 to from 10:1 are suitable for this purpose.

Most conveniently, reaction between the alkali metal 2-aminophenylglyoxylate and 1,1,1-trifluoroacetone is effected in the same reaction mixture in which the 2-aminophenylglyoxylate is produced from isatin, i.e., in an aqueous medium. However, if desired, any other inert liquid solvent can be employed. By an inert liquid solvent is meant a solvent which is nonreactive under the conditions of the reaction. Among such solvents are glacial acetic acid, dimethylformamide, dimethylsulfoxide, and alcohols such as methanol, ethanol, propanol, isopropanol, butanol, ehtylene glycol, propylene glycol, and the like. In general, an amount of solvent ranging from about 1 to about 100 times, preferably from about 1 to about 10 times, the weight of the reactants can be effectively employed.

Reaction between the alkali metal 2-aminophenylglyoxylate and 1,1,1-trifluoroacetone can be readily effected at temperatures between about 25° C. and 100° C., preferably between 50° C. and 75° C. However, higher or lower temperatures can be employed if desired.

Atmospheric pressure is usually employed in effecting reaction according to the process of the instant invention. However, pressures both above and below atmospheric pressure can also be employed whenever it is desirable to do so.

The following examples are set forth for purposes of illustration so that those skilled in the art may better understand the invention, and it should be understood that they are not to be construed as limiting this invention in any manner.

EXAMPLE 1

Preparation of 2-Trifluoromethyl Cinchoninic Acid

A 500 mL three-necked flask equipped with a stirrer, water condenser and thermometer was charged with fifteen grams (15 g) of isatin (0.10 mol), six grams (6 g) of potassium hydroxide (0.11 mol), and 100 mL of water. About 12 grams (12 g) of glacial acetic acid (0.20 mol) and 12 grams (12 g) of sodium acetate (0.14 mol) were then added to bring the pH of the mixture to 5±0.1. After the addition of 13.7 grams of trifluoroacetone (0.12 mol), the mixture was heated to 70° C. for 15 hours. At the end of this time, the mixture was acidified with 10% hydrochloric acid. A precipitate of 2-trifluoromethyl cinchoninic acid was obtained which was separated by filtration. The precipitate was washed with water until the wash water was clear, and then dried in air. About 18.8 grams of product was recovered, representing a yield of 76 percent.

EXAMPLE 2

Preparation of Potassium 2-Aminophenylglyoxylate

A 250 mL one-necked flask was charged with 18.3 grams of isatin (0.124 mol), 37.1 mL. of 30% potassium hydroxide (0.196 mol) and 50 mL of water. The mixture was stirred at room temperature for 6 hours. At the end of this time, the pH of the mixture was adjusted to 7.36 by the addition of 10% hydrochloric acid. Water was removed from the mixture by means of a rotary evaporator, and the crude potassium 2-aminophenylglyoxylate obtained in this manner was dried in a desicator. The crude, dried material weighed 22.1 grams, indicating a yield of 87 percent.

EXAMPLE 3

Preparation of 2-Trifluoromethyl Cinchoninic Acid

A one liter three-necked flask equipped with a magnetic bar, thermometer, and a water condenser attached to a cold trap containing isopropyl alcohol and dry ice, was charged with 35.6 grams of potassium 2-aminophenylglyoxylate (0.175 mol), 90 mL of water and 130 mL of ethanol, followed by the addition of 28.7 grams of sodium acetate (0.35 mol). A second mixture of 19.6 grams of trifluoroacetone (0.175 mol), 40 mL of water and 21.0 grams of acetic acid (0.35 mol) was then added to the first mixture in the reaction flask. The pH of the combined mixture was subsequently adjusted to 4.89 by the addition of an aqueous solution containing 50 percent by volume of acetic acid. The mixture was then heated at 67° C. for 18 hours. At the en of this time, the mixture had a pH of 4.46.

The hot solution was transferred into a 2 liter beaker, and then acidified with 10% hydrochloric acid until 2-trifluoromethyl cinchoninic acid precipitated from the mixture. The product was recovered by filtration. About 36.0 grams (0.149 mol) of product was obtained, representing a yield of 85 percent. The product was identified as 2-trifluoromethyl cinchoninic acid by infrared spectrometry.

What is claimed is:

1. In an improved method of preparing 2-trifluoromethyl cinchoninic acids of the formula:

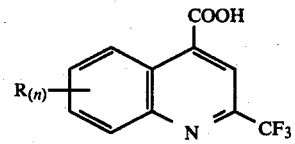

wherein R is selected from the group consisting of halogen, alkyl, aryl and alkoxy radicals, and n is an integer having a value of from 0 to 2, which comprises reacting an alkali metal 2-aminophenylglyoxylate of the formula:

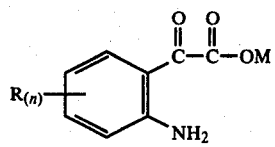

wherein M is an alkali metal, and R and n are as above defined, with 1,1,1-trifluoroacetone in the presence of an acid, the improvement comprising said acid being a weak acid, and said acid having an ionization constant between $1 \times 10^{-2}$ and $1 \times 10^{-7}$, and said reaction being effected in the presence of a metal salt of a weak acid, and the pH of the reaction mixture being between 3 and 6.

2. A method as in claim 1 wherein the pH of the reaction mixture is between 4.5 and 5.5.

3. A method as in claim 1 wherein the metal salt of a weak acid is an alkali metal salt.

4. A method as in claim 3 wherein the pH of the reaction mixture is between 4.5 and 5.5.

5. A method as in claim 1 or 2 wherein the alkali metal 2-aminophenylglyoxylate is potassium 2-aminophenylglyoxylate, the weak acid is acetic acid, and the metal salt of a weak acid is sodium acetate.

6. A method as in claim 1 wherein n is 0.

7. A method as in claim 6 wherein the pH of the reaction mixture is between 4.5 and 5.5.

8. A method as in claim 6 wherein the metal salt of a weak acid is an alkali metal salt.

9. A method as in claim 8 wherein the pH of the reaction mixture is between 4.5 and 5.5.

10. A method as in claim 6 or 7 wherein the alkali metal 2-aminophenylglyoxylate is potassium 2-aminophenylglyoxylate, the weak acid is acetic acid, and the metal salt of a weak acid is sodium acetate.

11. A method as in claim 1 wherein n has a value of from 1 to 2 and R contains from 1 to 6 carbon atoms when it is an alkyl, aryl or alkoxy group, and is chlorine when it is a halogen group.

12. A method as in claim 11 wherein the pH of the reaction mixture is between 4.5 and 5.5.

13. A method as in claim 11 wherein the metal salt of a weak acid is an alkali metal salt.

14. A method as in claim 13 wherein the pH of the reaction mixture is between 4.5 and 5.5.

15. A method as in claim 11 or 12 wherein the alkali metal 2-aminophenylglyoxylate is potassium 2-aminophenylglyoxylate, the weak acid is acetic acid, and the metal salt of a weak acid is sodium acetate.

16. In an improved method of preparing 2-trifluoromethyl cinchoninic acids of the formula:

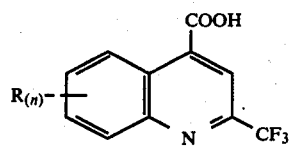

wherein R is selected from the group consisting of halogen, alkyl, aryl and alkoxy radicals, and n is an integer having a value of from 0 to 2, which comprises hydrolyzing an isatin compound of the formula:

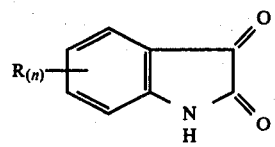

wherein R and n are as above defined in the presence of an alkali metal hydroxide, and then reacting the hydrolysis product with 1,1,1-trifluoroacetone in the presence of an acid, the improvement comprising said acid being a weak acid, and said acid having an ionization constant between $1 \times 10^{-2}$ and $1 \times 10^{-7}$, and said reaction being effected in the presence of a metal salt of a weak acid, and the pH of the reaction mixture being between 3 and 6.

17. A method as in claim 16 wherein the pH of the reaction mixture is between 4.5 and 5.5.

18. A method as in claim 16 wherein the metal salt of a weak acid is an alkali metal salt.

19. A method as in claim 18 wherein the pH of the reaction mixture is between 4.5 and 5.5.

20. A method as in claim 16 or 17 wherein the alkali metal hydroxide is potassium hydroxide, the weak acid is acetic acid, and the metal salt of a weak acid is sodium acetate.

21. A method as in claim 16 wherein n is 0.

22. A method as in claim 21 wherein the pH of the reaction mixture is between 4.5 and 5.5.

23. A method as in claim 21 wherein the metal salt of a weak acid is an alkali metal salt.

24. A method as in claim 23 wherein the pH of the reaction mixture is between 4.5 and 5.5.

25. A method as in claim 21 or 22 wherein the alkali metal hydroxide is potassium hydroxide, the weak acid is acetic acid, and the metal salt of a weak acid is sodium acetate.

26. A method as in claim 16 wherein n has a value of from 1 to 2 and R contains from 1 to 6 carbon atoms when it is an alkyl, aryl or alkoxy group, and is chlorine when it is a halogen group.

27. A method as in claim 26 wherein the pH of the reaction mixture is between 4.5 and 5.5.

28. A method as in claim 26 wherein the metal salt of a weak acid is an alkali metal salt.

29. A method as in claim 28 wherein the pH of the reaction mixture is between 4.5 and 5.5.

30. A method as in claim 26 or 27 wherein the alkali metal hydroxide is potassium hydroxide, the weak acid is acetic acid, and the metal salt of a weak acid is sodium acetate.

* * * * *